Nov. 13, 1973
Plant Pat. 3,407
G. K. McDANIEL
ROSE PLANT
Filed Jan. 27, 1972
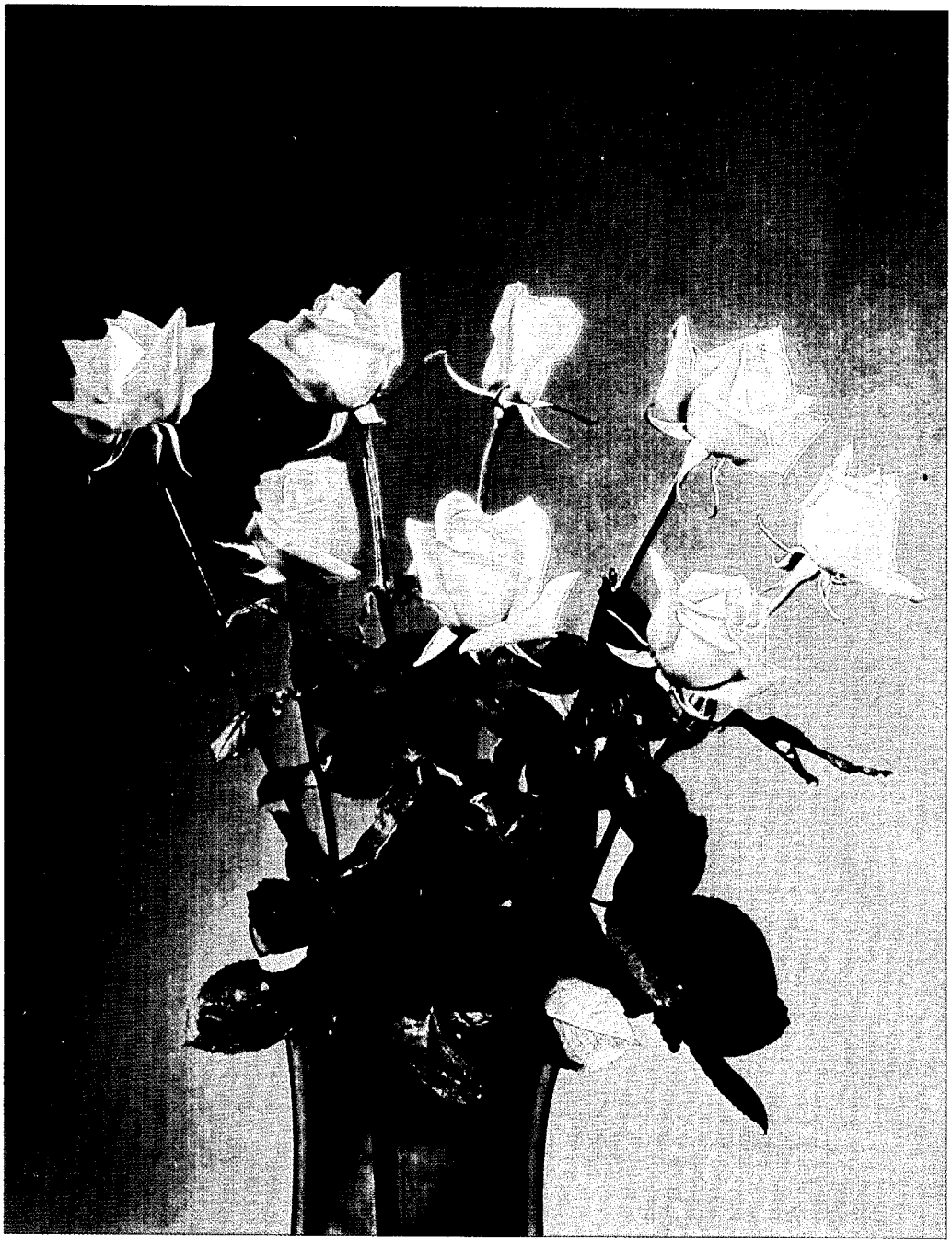

United States Patent Office

Plant Pat. 3,407
Patented Nov. 13, 1973

3,407
ROSE PLANT

Gayle Kent McDaniel, Carlton, Oreg., assignor to Carlton Rose Nurseries, Carlton, Oreg.

Filed Jan. 27, 1972, Ser. No. 221,457
Int. Cl. A01h 5/00
U.S. Cl. Plt.—20 1 Claim

ABSTRACT OF THE DISCLOSURE

A hybrid tea rose plant of the greenhouse type, of a distinctive orange color, originated by crossing an unnamed seedling (No. 39–B–67) as the seed parent, with an unnamed seedling (No. 44–E–66) as the pollen parent.

BACKGROUND OF DISCLOSURE

The present invention relates to a new and distinct variety of rose plant of the hybrid tea class, particularly for greenhouse growing for cut flowers, which was originated by me by crossing an unnamed seedling (No. 39–B–67), as the seed parent, with an unnamed seedling (No. 44–E–66), as the pollen parent.

The primary objective of this breeding was to produce a new rose variety of the distinctive color which would grow tall in the greenhouse for cut flowers and would combine the desirable qualities of its parents for this purpose.

Asexual reproduction of my new variety at Hillsboro, Oregon, shows that the characteristics come true to form and that the distinguishing characteristics hold through succeeding propagations by budding.

BRIEF DESCRIPTION OF DRAWINGS

The accompanying drawing shows typical specimens of the growth and flower of my new variety in different stages of development and as depicted in color as nearly true as it is possible to make the same in color illustrations of this character.

DETAILED DESCRIPTION OF DISCLOSURE

The following is a detailed description of my new variety, with color terminology in accordance with the Dictionary of Color by A. Maerz and M. Rea Paul.

Type: Hardy; bush; greenhouse; seedling; for cut flowers.
Class: Hybrid tea.
Propagation: It does hold its distinguishing characteristics through succeedling propagations by budding.

*Flower*

Locality where grown: Hillsboro, Oreg.
Flowers borne: Singly to stems; regular; on strong, long stems.
Quantity of bloom: Abundant, in greenhouse.
Continuity: Continuous.
Fragance: Moderate; tea.
Bud: Penduncle: long; heavy; stiff; green; entirely smooth.
*Before calyx breaks.*—Size: large. Form: long, pointed, with a conspicuous neck; with sometimes small appendages on the surface of the bud; sometimes with little foliaceous parts.
*As calyx breaks.*—Color: Troubador Red, Plate 3, L–8.
*As first petal opens.*—Size: large. Form: long, pointed. Color: Outside: Begonia Gaiety, Plate 2, K–8. Inside: Spark, Plate 2, L–10.
*Opening.*—It does open up well.
Bloom: Size when fully open: large, 4.5 inches to 5.5 inches.
*Petalage.*—Very double (many petals, usually with no stamens showing); 45 to 50 petals; arranged regularly.

*Form.*—High centered at first; petals remaining at first tightly rolled outward; becoming later at maturity loosely rolled outward.
Petals: Medium thick, soft; with inside velvety; outside satiny.
*Shape.*—Outer: obovate. Intermediate: obovate. Inner: obovate.

This description of a newly opened flower was made from a rose grown in a greenhouse in August 1971, at Hillsboro, Oreg.

*Color.*—Outer petal: Outside surface: Flirt, Plate 2, K–3; Inside surface: Pimento Chinese vermillion, Plate 2, L–11. Intermediate petal: Outside surface: Begonia Gaiety, Plate 2, K–8; inside surface: Pirate, Plate 2, K–11. Inner petal: Outside surface: Watermelon, Plate 1, K–9; inside surface: Castilian Red, Plate 1, L–10.

This description was made from a rose that was open for three days, indoors in a greenhouse in August 1971, at Hillsboro, Oreg.

*Color.*—Outer petal: Outside surface: Camellia, Plate 2, J–4; inside surface: Gladiolus, Plate 2, K–5. Inner petal: Outside surface: Casino Pink, Plate 1, I–4; inside surface: Flirt, Plate 2, K–9. General color effect: Newly opened flower: Begonia Gaiety, Plate 2, K–8 to Camellia, Plant 2, J–4 at center. Three days open: Begonia Gaiety, Plate 2, K–8 to Flirt, Plate 2, K–9.
*Behavior.*—Persist: lightens under high temperatures.
*Flower longevity.*—Cut roses grown in greenhouse kept at living room temperatures 7 days in August.

*Reproductive organs*

Stamens: Many; arranged regularly about pistils not mixed with petaloids.
Filaments: Many; most with anthers; short.
*Color.*—Red.
Anthers: Open at various times; medium.
*Color.*—Light yellow.
Seldom and anther fused with a petaloid.
Pollen: Moderate; yellow.
Pistils: many.
Styles: uneven; short; medium heavy; bunched.
Stigma: light yellow.
Ovaries: some protruding.
Hips: short; pear shaped; smooth; walls medium; green.
Sepals: permanent; medium long; straight spear shaped.
Seeds: medium number; medium size.

*Plant*

Foliage:
*Leaves.*—Compound of 3,5, many leaflets; normal; medium size; heavy.
*Leaflets.*—Shape: ovoid with apex acuminate, base obtuse with no serrations.
*Color.*—Mature—Upper surface: dark green; under surface: grey green. Young—Upper surface: light green; under surface: grey green.
*Rachis (the supporting stem of the compound leaf).*— medium weight. Upper side: Smooth with few minute hairs; under side: Glaborous.
*Stipules.*—Short, medium wide; short points; turning out at an angle of less than 45°.
*Disease.*—Resistant to mildew, blackspot.
Growth:
*Habit.*—Upright
*Growth.*—Vigorous.
*Canes.*—Medium weight.
*Main stems.*—Dull. Color: clear green. Prickles: none: Hairs: none.

*Branches.*—Dull. Color: clear green. Prickles: none. Hairs: none. New shoots: dull reddish green. Prickles: few, disappear as bud matures; color: light. Hairs: few; color: light. Thorns: several—right angle to slightly recurved, up to ½ in. sharp ochre in color.

I claim:

1. A new and distinct variety of rose plant of the hybrid tea class substantially as herein shown and described, characterized particularly as to its upright vigorous growth for cut flowers, with the novelty of the blooms characterized by distinctive shades of orange-red, which hold well indoors, and have moderate tea fragrance.

No references cited.

ROBERT E. BAGWILL, Primary Examiner